US012098176B2

(12) United States Patent
Yu et al.

(10) Patent No.: US 12,098,176 B2
(45) Date of Patent: Sep. 24, 2024

(54) KERATIN BD-4, PREPARATION METHOD, AND PHARMACEUTICAL COMPOSITION AND USE THEREOF

(71) Applicant: Institute of Materia Medica, Chinese Academy of Medical Sciences, Beijing (CN)

(72) Inventors: Shishan Yu, Beijing (CN); Xiaoliang Wang, Beijing (CN); Jing Qu, Beijing (CN); Mi Li, Beijing (CN); Guozhu Su, Beijing (CN); Ling Wang, Beijing (CN); Jie Cai, Beijing (CN); Shaofeng Xu, Beijing (CN); Jiang Fu, Beijing (CN)

(73) Assignee: Institute of Materia Medica, Chinese Academy of Medical Sciences, Beijing (CN)

( * ) Notice: Subject to any disclaimer, the term of this patent is extended or adjusted under 35 U.S.C. 154(b) by 0 days.

(21) Appl. No.: 17/771,994

(22) PCT Filed: Oct. 28, 2020

(86) PCT No.: PCT/CN2020/124329
§ 371 (c)(1),
(2) Date: Apr. 26, 2022

(87) PCT Pub. No.: WO2021/083193
PCT Pub. Date: May 6, 2021

(65) Prior Publication Data
US 2022/0372091 A1 Nov. 24, 2022

(30) Foreign Application Priority Data
Oct. 28, 2019 (CN) .......................... 201911028740.5

(51) Int. Cl.
| | | |
|---|---|---|
| *A61P 25/08* | (2006.01) | |
| *A61K 38/00* | (2006.01) | |
| *A61P 11/10* | (2006.01) | |
| *A61P 11/14* | (2006.01) | |
| *A61P 29/00* | (2006.01) | |
| *C07K 1/36* | (2006.01) | |
| *C07K 14/47* | (2006.01) | |
| *C12N 15/70* | (2006.01) | |

(52) U.S. Cl.
CPC .......... *C07K 14/4741* (2013.01); *A61P 11/10* (2018.01); *A61P 11/14* (2018.01); *A61P 25/08* (2018.01); *A61P 29/00* (2018.01); *C07K 1/36* (2013.01); *C12N 15/70* (2013.01); *A61K 38/00* (2013.01); *C12N 2800/101* (2013.01)

(58) Field of Classification Search
None
See application file for complete search history.

(56) References Cited

U.S. PATENT DOCUMENTS

| | | |
|---|---|---|
| 4,959,213 A | 9/1990 | Brod et al. |
| 5,994,081 A | 11/1999 | Tang et al. |
| 6,287,771 B1 | 9/2001 | Imamura et al. |
| 2007/0213717 A1 | 9/2007 | Trieu et al. |
| 2009/0047260 A1 | 2/2009 | Van Dyke |
| 2012/0009237 A1 | 1/2012 | Van Dyke |

FOREIGN PATENT DOCUMENTS

| | | |
|---|---|---|
| CN | 1324859 A | 12/2001 |
| CN | 101647814 A | 2/2010 |
| CN | 102993291 A | 3/2013 |
| CN | 104490929 | 4/2015 |
| CN | 105007894 | 10/2015 |
| CN | 109078023 A | 12/2018 |
| WO | 1999064066 A1 | 12/1999 |
| WO | 2014053038 A2 | 10/2014 |

OTHER PUBLICATIONS

Goncalves, et al., Antiviral therapies: advances and perspectives, Societe Francaisede Pharmacologie et de Therapeutique Fundamental & Clinical Pharmacology 35 (2021) 305-320. (Year: 2021).*
PCT International Search Report for PCT Application No. PCT/CN2020/124329 mailed Jan. 27, 2021 (10 pages, with English translation).
PCT Written Opinion for PCT Application No. PCT/CN2020/124329 mailed Jan. 27, 2021 (8 pages, with English translation).
Moore et al., "GenBank Accession No. BC142131, Version BC14131.1" NCBI GenBank, 2008.
Rieger et al., "Complete sequence of a bovine type I cytokeratin gene: conserved and variable intron positions in genes of polypeptides of the same cytokeratin subfamily," The EMBO Journal, 1985, 4(9):2261-2267.
Wu et al., "Effect of Antelope Horn Decoction on Serum TNF-α and IL-6 in Children with Persistent Fever," Chinese Journal of Ethnomedicine and Ethnopharmacy, 2018, 27(14), 4 pages, with English translation of abstract and 1st paragraph, left column, p. 79.
Zhang et al., "Research overview of the pharmacological action of Cornu Saigae Tataricae," China Medical Herald, 2013, 10(28), 13 pages, with partial English translation.
Antoine et al., Molecular forms of HMGB1 and keratin-18 as mechanistic biomarkers for mode of cell death and prognosis during clinical acetaminophen hepatotoxicity, Journal of Hepatology 2012 vol. 56, 1070-1079 (RETRACTED).

(Continued)

*Primary Examiner* — Thomas S Heard
(74) *Attorney, Agent, or Firm* — Merchant & Gould P.C.

(57) ABSTRACT

Provided are keratin BD-4, an encoding nucleic acid molecule thereof, an expression vector, a host cell, and a pharmaceutical composition containing the keratin. The keratin BD-4 can be used for preparing drugs having antipyretic and analgesic, antitussive and expectorant, and antiepileptic effects.

6 Claims, 2 Drawing Sheets

Specification includes a Sequence Listing.

(56) References Cited

OTHER PUBLICATIONS

Basit et al., "Health improvement of human hair and their reshaping using recombinant keratin K31", Biotechnology Reports, vol. 20, Oct. 24, 2018, page e00288, 6 pages.
Gao et al., "Recombinant Human Hair Keratin Nanoparticles Accelerate Dermal Wound Healing", Applied Materials & INTERFACES, vol. 11, No. 20, May 22, 2019, p. 18681-18690.
Guo et al., "Recombinant human hair keratin proteins for halting bleeding", Artificial Cells, Nanomedicine and Biotechnology, vol. 46, No. sup2, Apr. 6, 2018, pp. 456-461.
"Keratin, type I cuticular Ha5, Bos indicus x Bos taurus (Hybrid cattle)", XP093088441, Database accession No. A0A4W2E4E4 Database UniProtKB [Online] Sep. 18, 2019, 6 pages.
"KRT33A protein (Bos taurus) ", XP093086960, Database accession No. A5PJJ1 Database UniProtKB [Online] Jul. 10, 2007, 6 pages.
Liu et al., "Peptidome characterization of the antipyretic fraction of Bubali Cornu aqueous extract by nano liquid chromatography with orbitrap mass spectrometry detection", Journal of Separation Science, vol. 40, No. 2, Jan. 25, 2017, pp. 587-595.
Moore et al., "KRT33A protein (Bos taurus) ", Database accession No. AAI42132.1, Database, National Library of Medicine. Jun. 9, 2008, 3 pages.
Moore et al., "GenBank Accession No. AA142132, Version AA142132.1" NCBI GenBank, Jun. 9, 2008, 3 pages.
Extended European Search Report dated Oct. 20, 2023 for EP Application No. EP20881931 (13 pages).
Wiener et al., "Novel Features of the Prenatal Horn Bud Development in Cattle (Bos taurus)", PLOS One, vol. 10, No. 5, May 20, 2015, page e0127691, 13 pages.
Yuanxun et al., "Chinese molecular traditional Chinese pharmacy", Chinese Molecular Medicine Series, 2017, 6 pages. (Chinese).

\* cited by examiner

SEQUENCE LISTING

<160> NUMBER OF SEQ ID NOS: 2

<210> SEQ ID NO 1
<211> LENGTH: 401
<212> TYPE: PRT
<213> ORGANISM: Bos taurus

<400> SEQUENCE: 1

```
Met Ser Tyr Ser Cys Cys Leu Pro Asn Leu Ser Phe Arg Ser Ser Cys
1               5                   10                  15

Ser Ser Arg Pro Cys Val Pro Ser Ser Cys Cys Gly Thr Thr Leu Pro
            20                  25                  30

Gly Ala Cys Asn Ile Pro Ala Asn Val Gly Ser Cys Asn Trp Phe Cys
        35                  40                  45

Glu Gly Ser Phe Asn Gly Ser Glu Lys Glu Thr Met Gln Phe Leu Asn
    50                  55                  60

Asp Arg Leu Ala Ser Tyr Leu Glu Lys Val Arg Gln Leu Glu Arg Asp
65                  70                  75                  80

Asn Ala Glu Leu Glu Ser Arg Ile Leu Glu Arg Ser Gln Gln Gln Glu
                85                  90                  95

Pro Leu Val Cys Pro Asn Tyr Gln Ser Tyr Phe Arg Thr Ile Glu Glu
            100                 105                 110

Leu Gln Gln Lys Ile Leu Cys Ser Lys Ser Glu Asn Ala Arg Leu Val
        115                 120                 125

Val Gln Ile Asp Asn Ala Lys Leu Ala Ser Asp Asp Phe Arg Thr Lys
    130                 135                 140

Tyr Glu Thr Glu Val Ser Leu Arg Gln Leu Val Glu Ala Asp Leu Asn
145                 150                 155                 160

Gly Leu Arg Arg Ile Leu Asp Glu Leu Thr Leu Cys Lys Ser Asp Leu
                165                 170                 175

Glu Ala Arg Val Glu Ser Leu Lys Glu Glu Leu Ile Cys Leu Lys Gln
            180                 185                 190

Asn His Glu Gln Glu Val Asn Thr Leu Arg Ser Gln Leu Gly Asp Arg
```

```
                195                 200                 205
Leu Asn Val Glu Val Asp Ala Ala Pro Thr Val Asp Leu Asn Arg Val
    210                 215                 220
Leu Asn Glu Thr Arg Ala Gln Tyr Glu Ala Leu Val Glu Thr Asn Arg
225                 230                 235                 240
Arg Asp Val Glu Glu Trp Tyr Ile Arg Gln Thr Glu Glu Leu Asn Lys
                245                 250                 255
Gln Val Val Ser Ser Glu Gln Leu Gln Ser Tyr Gln Ala Glu Ile
            260                 265                 270
Ile Glu Leu Arg Arg Thr Val Asn Ala Leu Glu Val Glu Leu Gln Ala
            275                 280                 285
Gln His Asn Leu Arg Asp Ser Leu Glu Asn Thr Leu Thr Glu Thr Glu
        290                 295                 300
Ala Arg Tyr Ser Cys Gln Leu Ala Gln Val Gln Gly Leu Ile Gly Asn
305                 310                 315                 320
Val Glu Ser Gln Leu Ala Glu Ile Arg Ser Asp Leu Glu Arg Gln Asn
                325                 330                 335
Gln Glu Tyr Gln Val Leu Leu Asp Val Arg Ala Arg Leu Glu Cys Glu
            340                 345                 350
Ile Asn Thr Tyr Arg Gly Leu Leu Asp Ser Glu Asp Cys Lys Leu Pro
        355                 360                 365
Cys Asn Pro Cys Ala Thr Thr Asn Ala Cys Glu Arg Pro Cys Ile Ser
370                 375                 380
Asn Pro Cys Val Ser Arg Ala Arg Cys Gly Pro Cys Asn Thr Phe Val
385                 390                 395                 400
His
```

<210> SEQ ID NO 2
<211> LENGTH: 1206
<212> TYPE: DNA
<213> ORGANISM: Bos taurus

<400> SEQUENCE: 2

```
atgtcgtaca gttgctgtct tccaaatctg tcattccgct cctcttgtag tagccgtcct      60
tgcgtcccct caagctgctg cggcacgacc ctgcctggag catgcaacat tcctgccaac     120
gtcgggagct gtaactggtt ttgcgaggga agtttcaacg gcagcgagaa ggagactatg     180
caattcctga atgatcgcct ggcatcctac ttggaaaaag tccggcaatt ggagcgtgac     240
aacgccgagt tggagtcccg gatcttggaa cggtctcagc aacaggagcc tttggtttgc     300
ccaaactacc aaagctactt tcggacgatc gaagagttgc agcagaagat actgtgcagt     360
aagtcggaaa acgcacgttt ggtggtccag attgataacg cgaagctggc ttccgacgac     420
ttccgcacaa agtacgaaac ggaggttagc ttgcgccagt tggttgaggc ggaccttaac     480
gggctgcgcc gtatcctgga tgagttgacg ctgtgcaagt ctgacctgga agcgcgggta     540
gaatcgttga aggaagagct gatatgcctg aagcagaacc acgagcagga agtgaatacg     600
cttcggtcgc aacttggtga ccggttgaac gtggaggtgg atgctgcccc gaccgtcgat     660
ttgaaccgcg tcttgaatga gaccgtgcg cagtatgagg cactggtgga aacaaatcgg     720
cgtgacgtgg aagaatggta catccgccaa accgaagaat aaacaagca ggtcgtctct     780
agcagcgaac aactgcagag ttaccaggcc gagatcattg agttgcgccg gaccgtgaac     840
gctttggagg tcgaactgca agcgcaacat aaccttcgcg acagtcttga aacacactg     900
acggagaccg aggcgcggta ttcttgtcag cttgcccagg ttcagggact tatcgggaac     960
```

```
                                                            -continued gttgagagcc agttagcgga aatccgcagc gaccttgagc ggcagaatca agagtaccag    1020
gtccttctgg acgtgcgggc tcgccttgag tgtgagatta atacgtaccg cggattgttg    1080
gattcggaag actgcaaatt gccatgtaac ccctgcgcca ctacgaatgc gtgcgaacgc    1140
ccgtgcatta gcaacccatg cgtctcgcgt gcgcgttgcg gcccgtgtaa tacctttgtc    1200
cattaa                                                               1206
```

KERATIN BD-4, PREPARATION METHOD, AND PHARMACEUTICAL COMPOSITION AND USE THEREOF

CROSS-REFERENCE TO RELATED APPLICATIONS

This application is a National Stage Application of PCT/CN2020/124329, filed 28 Oct. 2020, which claims benefit of Serial No. 201911028740.5, filed 28 Oct. 2019 in China and which applications are incorporated herein by reference. To the extent appropriate, a claim of priority is made to each of the above disclosed applications.

SEQUENCE STATEMENT

This application contains a Sequence Listing, which has been submitted electronically in ASCII format and is hereby incorporated by reference in its entirety. Said ASCII copy, created and filed in PCT/CN2020/124329, is named Sequence_Listing.txt and is 8,192 bytes (8.00 KB) in size.

TECHNICAL FIELD

The present invention relates to a keratin BD-4, a nucleic acid molecule encoding keratin BD-4, an expression vector containing the nucleic acid molecule, a host cell containing the expression vector or genome integrating the nucleic acid molecule, preparation methods of keratin BD-4 and pharmaceutical compositions containing this keratin. Further, the keratin and the pharmaceutical composition are used in the preparation of medicaments for antipyretic, analgesic, antitussive expectorant, anticonvulsant, antiepileptic, hypotensive, anti-inflammatory, and antiviral.

BACKGROUND TECHNIQUE

Keratin is a kind of protein, which is widely found in the epidermis of humans and animals, and is the main component of hair, feathers, hoofs, shells, claws, horns, etc. It is an extremely important structural protein for connective tissue and plays a role in protecting the body.

Keratin is widely present in organisms and is a renewable resource with great utilization value, but it has not been widely and effectively used. The main reason is that keratin is insoluble in various solvents, and keratin is generally more resistant to enzymatic hydrolysis by proteases than other proteins. Therefore, it is very difficult to extract and prepare natural keratin.

With the rapid development of modern biotechnology such as genomics, proteomics, genetic engineering, and microbial engineering, more and more genes have been discovered. The use of protein expression systems to prepare and produce target proteins is an important method for studying the biological functions of genes or proteins.

SUMMARY OF THE INVENTION

The technical problem solved by the present invention is to provide a keratin BD-4, a nucleic acid molecule encoding keratin BD-4, an expression vector containing the nucleic acid molecule, and a host cell containing the expression vector or genome integrating the nucleic acid molecule, and The preparation methods of keratin BD-4, the pharmaceutical compositions containing keratin BD-4, and the above-mentioned keratin BD-4, nucleic acid molecule, expression vector, host cell, or pharmaceutical compositions are used in the preparation of antipyretic, analgesic, and antitussive Application in expectorant, anticonvulsant, antiepileptic, blood pressure lowering, anti-inflammatory and antiviral drugs.

In order to solve the technical problems of the present invention, the present invention provides the following technical solutions:

The first aspect of the technical solution of the present invention in is to provide a keratin BD-4, characterized in that the amino acid sequence of the keratin BD-4 is:

(1) The amino acid sequence shown in SEQ ID NO: 1 in the sequence listing.

(2) The amino acid sequence shown in SEQ ID NO: 1 in the sequence listing is formed by substitution, deletion or addition of 1-35 amino acids to form an amino acid sequence that basically maintains the same biological function.

Further, conventional modification can be performed on keratin BD-4; or a label for detection or purification can be attached to keratin BD-4.

Furthermore, the conventional modifications include acetylation, amidation, cyclization, glycosylation, phosphorylation, alkylation, biotinylation, fluorescent group modification, polyethylene glycol PEG modification, immobilization modification, Sulfation, oxidation, methylation, deamination, formation of disulfide bonds or rupture of disulfide bonds; The labels include His6, GST, EGFP, MBP, Nus, HA, IgG, FLAG, c-Myc, Profinity eXact.

The second aspect of the technical solution of the present invention provides a nucleic acid molecule encoding the keratin BD-4 of the first aspect.

Further, the nucleotide sequence of the nucleic acid molecule is:

(1) The nucleotide sequence shown in SEQ ID NO: 2 in the sequence listing.

(2) The nucleotide sequences obtained by sequence optimization based on the nucleotide sequence shown in SEQ ID NO: 2.

(3) The nucleotide sequences complementary to the nucleotide sequence in (1) or (2) above.

The third aspect of the technical solution of the present invention provides an expression vector, which is characterized in that the expression vector contains the nucleic acid molecule described in the second aspect.

Further, the expression vector can be pET series, pUC series, pQE series, pBV series, pMAL series, pPIC9, pPIC9K, pHIL-S1, pPICZα/A, pYAM75P, pHIL-D2, pA0815, pPIC3K, pPICZ, pHWO10, pGAPZ, pGAPZa, pPIC3.5K, etc.; the preferred expression vector is the pET series vector; the most preferred expression vector is pET-28a(+).

The fourth aspect of the technical solution of the present invention provides a host cell, characterized in that the host cell contains the expression vector of the third aspect or the nucleic acid molecule of the second aspect is integrated into the genome.

Further, the host cell includes bacteria, yeast, *aspergillus*, plant cells, or insect cells.

Furthermore, the bacteria include *Escherichia coli* or yeast.

Competent host cells can be BL21 series, Transetta series, Rosetta series, DH5α series, JM series, Top series, Orgami series, Trans1-T1, TG1, TB1; Y11430, MG1003, GS115 (AOX1), KM71, SMD1168, etc.; The preferred expression competent cells are BL21 (DE3), Transetta (DE3).

The fifth aspect of the technical solution of the present invention provides a method for preparing the keratin BD-4 of the first aspect, which is characterized in that it comprises the following steps:

A. Synthesize the nucleic acid molecule corresponding to the keratin BD-4 described in the first aspect, link the nucleic acid molecule into the corresponding expression vector, and transform the expression vector into the host cell. Culture host cells with expression vector in fermentation equipment under certain conditions and induce expression of keratin BD-4 to obtain a crude protein solution containing keratin BD-4.

B. The crude protein solution expressed in step A is separated, purified and dried to obtain keratin BD-4.

Further, in step A, the host cells are mainly selected from *Escherichia coli*, the keratin BD-4 is expressed in *Escherichia coli* inclusion bodies, and the fermentation equipments include shaker flasks or fermenters.

Further, in step A, after the expression of keratin BD-4 is induced, the impurities can be washed with cleaning agents and dissolved in a solution to obtain a crude protein solution.

Further, the medium in step A may be LB medium, TB medium, SB medium, SOB medium, SOC medium, PDA medium, YPD medium, red bengal medium, high salt Chashi medium, DOBA medium, rice koji medium and its modified formula, etc.; shake flask fermentation preferably LB medium, TB medium, most preferably TB medium; fermenter preferably LB medium and its modified formula.

Further, the inducer in step A can be IPTG, lactose, arabinose, etc.; Preferred are IPTG and lactose.

Further, in step A, the obtained fermentation broth is centrifuged and then the supernatant is discarded; The precipitate is suspended in the buffer, the bacteria are broken, centrifuged again, and the supernatant is discarded; After the precipitate is washed with a detergent, it is then dissolved in a urea solution to obtain a BD-4 crude protein solution.

Among them, the buffer is preferably buffer A, and its dosage is: fermentation broth volume:buffer A volume=1~100:1, preferably 10:1;

The cleaning agent can be urea solution, guanidine hydrochloride solution, triton and buffer A, etc., preferably urea solution, most preferably 2M urea solution (may contain 1% Triton). The dosage is: fermentation broth volume: 2M urea volume=0.2~100:1, preferably 1~15:1;

The urea solution is preferably the 8M urea solution, and its dosage is: the volume of the fermentation broth: 8M urea volume=0.2~100:1, preferably 2~15:1.

Further, in step B, the separation and purification method includes ultrafiltration microfiltration membrane technology purification method, column chromatography purification method, salting out method, and dialysis method.

Further, in step B, the separation and purification method is as follows:

(1) The dialysis method is to purify the crude protein solution obtained in step A by a dialysis method to obtain the target protein BD-4 solution.

The molecular weight cut-off of the dialysis bag can be 0.5-10 kD, the preferred molecular weight cut-off of the dialysis bag is 3.5-10 kD, and the most preferred molecular weight cut-off of the dialysis bag is 10 kD.

(2) In the ultrafiltration and microfiltration method, the crude protein solution obtained in step A is purified by membrane technology such as ultrafiltration membrane or microfiltration membrane to obtain a concentrated solution of the target protein BD-4.

Preferably, the microfiltration membrane purification is performed twice, the first time the membrane pore size is 1000~1500 nm, and the second time the membrane pore size is 20~50 nm.

(3) The column chromatography method is to pass the crude protein solution obtained in step A through column chromatography, such as various exchange columns or exclusion column chromatography, to separate and purify the target protein BD-4.

The preferred exclusion column is dextran gel column, Superdex 30 Increase, Superdex 75 Increase, Superdex 200 Increase and Superose 6 Increase, etc.;

The preferred exchange column is an ion exchange resin column: anion exchange resin column: HiTrap Q FF, HiTrap Capto Q ImpRes, Capto Q ImpRes, HiTrap Capto Q, HiTrap DEAE, Toyopearl Q-650M and Toyopearl SuperQ-650M, etc.; Cation exchange resin column: HiTrap SP FF, HiTrap Capto SP ImpRes, Capto SP ImpRes, HiTrap Capto SP, Toyopearl SP-650M and Toyopearl Super SP-650M. The most preferred is an anion exchange resin column.

As the eluent, commonly used eluents in the art can be used, such as water and salt solution. The salt solution includes sodium chloride solution, sodium dihydrogen phosphate solution, disodium hydrogen phosphate solution, sodium acetate, acetic acid, and the like.

(4) The salting-out method is to purify the crude protein solution obtained in step A by salting-out method to obtain the target protein BD-4 suspension.

The salting-out agent can be ammonium sulfate, sodium sulfate, sodium chloride, magnesium chloride, aluminum sulfate, ammonium nitrate, ammonium chloride, magnesium sulfate, and the like. The preferred salting-out agent is ammonium sulfate and its aqueous solution. A saturated aqueous solution of ammonium sulfate is added to make the final concentration of ammonium sulfate reach 10-50%, preferably 20-30%, more preferably 25%.

The number of salting out is 1 to 3 times, preferably 2 times.

After salting out, the precipitate is washed with pure water, and the washing frequency is 2 to 5 times, preferably 3 times.

Further, the target protein BD-4 solution purified in step B can be freeze-dried or vacuum-dried into a dry powder, or the concentrated solution can be directly spray-dried into a dry powder.

The sixth aspect of the technical solution of the present invention provides a pharmaceutical composition, characterized in that the pharmaceutical composition contains the keratin BD-4 described in the first aspect or the nucleic acid molecule described in the second aspect or the first expression vector of the third aspect or the host cell of the fourth aspect and a pharmaceutically acceptable carrier or excipient.

The keratin obtained in the above steps of the present invention can be freeze-dried or vacuum-dried into a dry powder, or the concentrated liquid can be directly spray-dried into a dry powder, and then made into various dosage forms.

The present invention relates to a pharmaceutical composition, which comprises any keratin obtained in the above steps and a pharmaceutically acceptable carrier.

The present invention also relates to a pharmaceutical composition containing the keratin of the present invention as an active ingredient and conventional pharmaceutical excipients or adjuvants. Generally, the keratin of the present invention accounts for 0.1-100.0% of the total weight of the pharmaceutical composition.

The present invention also provides a pharmaceutical composition, which includes a pharmaceutical effective dose of protein as an active ingredient and a pharmaceutically acceptable carrier.

The pharmaceutical composition of the present invention can be prepared according to methods recognized in the field. When used for this purpose, if necessary, the protein of the present invention can be combined with one or more solid or liquid pharmaceutical excipients and/or adjuvants to prepare an appropriate administration form or dosage that can be used as human or Veterinary drugs form.

The keratin of the present invention or the pharmaceutical composition containing it can be administered in a unit dosage form. The route of administration can be enteral or parenteral, such as oral administration, intramuscular, subcutaneous, nasal cavity, oral mucosa, eyes, lungs, skin, vagina, peritoneum and rectum, etc., oral administration is preferred.

The keratin protein of the present invention or the pharmaceutical composition containing it can be administered by injection. Injections include intravenous injection, intramuscular injection, subcutaneous injection, intradermal injection, intraperitoneal injection, and acupoint injection, etc.

The dosage form for administration may be a liquid dosage form, a solid dosage form or a semi-solid dosage form. Liquid dosage forms can be solutions (including true solutions and colloidal solutions), emulsions (including oil-in-water, water-in-oil and double emulsions), suspensions, injections (including water injections, powder injections and infusions), eye drops Lotion, nasal drops, lotion and liniment, etc. The solid dosage form can be tablets (including ordinary tablets, enteric-coated tablets, buccal tablets, dispersible tablets, chewable tablets, effervescent tablets, orally disintegrating tablets), capsules (including hard capsules, soft capsules, and enteric-coated capsules), granules Preparations, powders, pellets, dripping pills, suppositories, films, patches, air (powder) sprays, sprays, etc.; semi-solid dosage forms can be ointments, gels, pastes, etc.

The keratin of the present invention can be made into ordinary preparations, slow-release preparations, controlled-release preparations, targeted preparations, and various particle delivery systems.

In order to make a unit dosage form into a tablet, various excipients known in the art can be widely used, including diluents, binders, wetting agents, disintegrants, lubricants and glidants. The diluent can be starch, dextrin, sucrose, glucose, lactose, mannitol, sorbitol, xylitol, microcrystalline cellulose, calcium sulfate, calcium hydrogen phosphate, calcium carbonate, etc.; the humectant can be water, ethanol, iso Propanol, etc.; the binder can be starch syrup, dextrin, syrup, honey, glucose solution, microcrystalline cellulose, acacia syrup, gelatin syrup, sodium carboxymethyl cellulose, methyl cellulose, hypromellose Base cellulose, ethyl cellulose, acrylic resin, carbomer, polyvinylpyrrolidone, polyethylene dipropanol, etc.; disintegrant can be dry starch, microcrystalline cellulose, low-substituted hydroxypropyl cellulose, Cross-linked polyvinylpyrrolidone, cross-linked sodium carboxymethyl cellulose, sodium carboxymethyl starch, sodium bicarbonate and rafter acid, calcium carbonate, polyoxyethylene sorbitol fatty acid ester, dodecyl Sodium sulfonate; lubricant and glidant can be talc, silicon dioxide, stearate, tartaric acid, liquid paraffin, polyethylene glycol, etc.

The tablets can also be further made into coated tablets, such as sugar-coated tablets, film-coated tablets, enteric-coated tablets, or double-layer tablets and multi-layer tablets.

In order to make the administration unit into a pill, various carriers known in the field can be widely used. Examples of carriers are, for example, diluents and absorbents, such as glucose, lactose, starch, cocoa butter, hydrogenated vegetable oil, polyvinylpyrrolidone, polyethylene glycol laurate, kaolin, talc, etc.; binders, such as Gum arabic, xanthan gum, gelatin, ethanol, honey, liquid sugar, rice paste or batter, etc.; disintegrants, such as agar powder, dried starch, alginate, sodium lauryl sulfonate, methyl cellulose, ethyl cellulose and so on.

In order to make the administration unit into a suppository, various carriers known in the field can be widely used. Examples of carriers are, for example, polyethylene glycol, lecithin, cocoa butter, higher alcohols, higher alcohol esters, gelatin, semi-synthetic glycerides and the like.

In order to make the dosing unit into a capsule, the active ingredient keratin of the present invention is mixed with the above-mentioned various carriers, and place the resulting mixture in hard gelatin capsules or soft capsules. The active ingredient keratin of the present invention can also be made into microcapsules, suspended in an aqueous medium to form a suspension, or filled into hard capsules or made into injections for application.

For example, the keratin of the present invention is prepared into injection preparations, such as solutions, suspension solutions, emulsions and freeze-dried powder injections. Such preparations may be aqueous or non-aqueous, and may contain one and/or more pharmacodynamically acceptable carriers, diluents, binders, lubricants, preservatives, surfactants or dispersants. For example, the diluent can be selected from water, ethanol, polyethylene glycol, 1,3-propylene glycol, ethoxylated isostearyl alcohol, polyoxylated isostearyl alcohol, polyoxyethylene sorbitol fatty acid esters and the like. In addition, in order to prepare an isotonic injection, an appropriate amount of sodium chloride, glucose or glycerin can be added to the injection preparation. In addition, conventional solubilizers, buffers, pH adjusters, etc. can also be added. These auxiliary materials are commonly used in this field.

In addition, if necessary, coloring agents, preservatives, flavors, flavors, sweeteners or other materials can also be added to the pharmaceutical preparations.

In order to achieve the purpose of medication and enhance the therapeutic effect, the keratin or the pharmaceutical composition of the present invention can be administered by any known administration method.

The dosage of the keratin pharmaceutical composition of the present invention depends on many factors, such as the nature and severity of the disease to be prevented or treated, the gender, age, weight, personality and individual response of the patient or animal, the route of administration, the number of administrations and the purpose of treatment, so the therapeutic dose of the present invention can have a wide range of changes. Generally speaking, the dosage of the pharmaceutical ingredients of the present invention is well known to those skilled in the art. Appropriate adjustments can be made according to the actual amount of the drug contained in the final preparation in the keratin composition of the present invention to meet the requirement of the therapeutically effective amount and accomplish the preventive or therapeutic purpose of the present invention. The appropriate daily dosage range of keratin of the present invention: the dosage of keratin of the present invention is 0.01~500 mg/kg body weight. It is preferably 0.5~ 100 mg/kg body weight, more preferably 1~ 50 mg/kg body weight, and most preferably 2~30 mg/kg body weight. The above dosage can be administered in a single dosage form or divided into several, such as two, three or four dosage forms, depending on the clinical experience of the administering doctor and the dosage regimens including the use of other treatments. The total dose required for each treatment can be divided into multiple or single doses. The protein or pharmaceutical composition of the present invention can be taken alone, or use it in combination with other therapeutic drugs or symptomatic drugs and adjust the dose.

The seventh aspect of the technical solution of the present invention provides the use of the keratin BD-4 according to the first aspect or the nucleic acid molecule according to the second aspect or the expression vector according to the third aspect or the host cell according to the fourth aspect or the pharmaceutical composition according to the sixth aspect in the preparation of medicaments for antipyretic, analgesic, antitussive, expectorant, anticonvulsant, antiepileptic, hypotensive, anti-inflammatory, or antiviral.

In order to accomplish the purpose of the present invention, the present invention takes the following technical solutions. Specifically, the preparation of keratin BD-4 of the present invention includes the following steps:

(1) Synthesize the nucleotide sequence and determine the accuracy of the sequence;

The preferred nucleotide sequence is shown in SEQ ID NO: 2.

(2) Transfer the nucleotide sequence into an expression vector;

The expression vector can be pET series, pUC series, pQE series, pBV series, pMAL series, pPIC9K, pHIL-S1, pPICZα/A, pYAM75P, pHIL-D2, pA0815, pPIC3K, pPICZ, pHWO10, pGAPZ, pGAPZa, pPIC3.5K, etc. The preferred expression vector is the pET series vector; the most preferred expression vector is pET-28a(+).

(3) Transfection of expression vector into host cell;

The host cell can be *E. coli* or yeast; the preferred host cell is *E. coli*;

Competent cells can be BL21 series, Transetta series, Rosetta series, DH5α series, JM series, Top series, Orgami series, Trans1-T1, TG1, TB1; Y11430, MG1003, GS115 (AOX1), KM71, SMD1168, ect. Preferred expression competent cells are BL21 (DE3) and transetta (DE3).

(4) The host cells will be fermentation culture to induce the expression of the target protein BD-4 under appropriate conditions;

Fermentation equipment can use shake flasks or fermentation tanks;

The medium can be LB medium, TB medium, SB medium, SOB medium, SOC medium, PDA medium, YPD medium, red bengal medium, high salt Chashi medium, DOBA medium, rice koji culture medium and their improved formulas, etc.; Shake flask fermentation is preferably LB medium, TB medium, and most preferably TB medium; fermenter preferably LB medium and its improved formulas.

The inducer can be IPTG, lactose, arabinose, etc.; The preferred are IPTG and lactose.

(5) Target protein BD-4 product enrichment;

Centrifuge the fermentation broth obtained in step (4), and discard the supernatant; The precipitate is suspended in the buffer, the bacteria are broken, centrifuged again, and the supernatant is discarded; After the precipitation is washed with detergents, it is dissolved in a urea solution to obtain a BD-4 crude protein solution.

Among them, the buffer is preferably buffer A, and its dosage is: fermentation broth volume:buffer A volume=1~100:1, preferably 10:1;

The cleaning agent can be urea solution, guanidine hydrochloride solution, Triton, buffer A, etc., preferably urea solution, most preferably 2M urea solution (may contain 1% Triton). The dosage is fermentation broth volume: 2M urea volume=0.2~100:1, preferably 1~15:1;

The urea solution is preferably an 8M urea solution. Its dosage is the volume of the fermentation broth: 8M urea volume=0.2~100:1, preferably 2~15:1.

(6) Separation and purification of target protein BD-4.

The crude protein solution obtained in step (5) needs to be purified to obtain the target protein BD-4. The purification can be carried out by dialysis, or ultrafiltration and microfiltration, or column chromatography, or salting out steps.

A. In the dialysis step, the crude protein solution obtained in step (5) is purified by a dialysis method to obtain the target protein BD-4 solution.

The molecular weight cut-off of the dialysis bag can be 0.5-10 kD, the preferred molecular weight cut-off of the dialysis bag is 3.5-10 kD, and the most preferred molecular weight cut-off of the dialysis bag is 10 kD.

B. In the ultrafiltration and microfiltration step, the crude protein solution obtained in step (5) is purified by membrane technology such as ultrafiltration membrane or microfiltration membrane to obtain the target protein BD-4 concentrated solution.

Preferably, the microfiltration membrane purification is performed twice. the first time the membrane pore size is 1000~1500 nm, and the second time the membrane pore size is 20~50 nm.

C. In the column chromatography step, the crude protein solution obtained in step (5) is passed through column chromatography, such as various exchange columns or exclusion column chromatography, to separate and purify the target protein BD-4.

The preferred exclusion column is dextran gel column, Superdex 30 Increase, Superdex 75 Increase, Superdex 200 Increase, Superose 6 Increase, etc.; The preferred exchange column is an ion exchange resin column: anion exchange resin column, HiTrap Q FF, HiTrap Capto Q ImpRes, Capto Q ImpRes, HiTrap Capto Q, HiTrap DEAE, Toyopearl Q-650M, Toyopearl SuperQ-650M, etc.; Cation exchange resin column, HiTrap SP FF, HiTrap Capto SP ImpRes, Capto SP ImpRes, HiTrap Capto SP, Toyopearl SP-650M, Toyopearl Super SP-650M. The most preferred is an anion exchange resin column.

As the eluent, commonly used eluents in the art can be used, such as water, salt solution, and the salt solution includes sodium chloride solution, sodium dihydrogen phosphate solution, disodium hydrogen phosphate solution, sodium acetate, acetic acid, and the like.

D. The salting-out step is to purify the crude protein solution obtained in step (5) by a salting-out method to obtain the target protein BD-4 suspension.

The salting-out agent can be ammonium sulfate, sodium sulfate, sodium chloride, magnesium chloride, aluminum sulfate, ammonium nitrate, ammonium chloride, magnesium sulfate, and the like. The preferred salting-out agent is ammonium sulfate and its aqueous solution. A saturated aqueous solution of ammonium sulfate is added to make the final concentration of ammonium sulfate reach 10-50%, preferably 20-30%, more preferably 25%.

The number of salting out is 1 to 3 times, preferably 2 times.

After salting out, the precipitate is washed with pure water, and the washing frequency is 2 to 5 times, preferably 3 times.

The target protein BD-4 solution purified from steps A to D can be freeze-dried or vacuum dried into dry powder, or the concentrated solution can be directly spray-dried into dry powder.

The beneficial technical effects of the present invention:

1. The protein of the present invention is the keratin obtained for the first time, and the preparation method of the present invention has the characteristics of high yield and high sample purity.

2. In the present invention, through the pharmacodynamic test study of protein BD-4 on lipopolysaccharide (LPS) and yeast induced fever model in SD rats, it is proved that the protein BD-4 can significantly inhibit the increase of body temperature and has a significant antipyretic effect 4 hours and 8 hours after the yeast is modeled;

3. In the present invention, the pharmacodynamic test study of protein BD-4 on pilocarpine (PLO) and Pentylenetetrazole (PTZ) induced convulsions and epilepsy in mice respectively, proved that protein BD-4 can significantly prolong the incubation period of class II and class III epilepsy in mice.

4. The present invention proves that the protein BD-4 has obvious expectorant effect through the pharmacodynamic test study of the protein BD-4 on the phenol red excretion method in mice;

5. In the present invention, the pharmacodynamic study of protein BD-4 on the antitussive effect of the method of inducing cough with ammonia water in mice proves that the protein BD-4 can significantly reduce the number of coughs and prolong the incubation period of coughs and has a significant antitussive effect;

6. The present invention proves that the protein BD-4 can significantly reduce the number of writhing times in mice and has a significant analgesic effect. through the pharmacodynamic test study of the protein BD-4 on the acetic acid writhing of ICR mice.

FIGURE DESCRIPTION

(M: Protein molecular weight standard; S: Expressed protein)

(Compared with normal control group, $P<0.01$, *$P<0.001$; Compared with the model group, #$P<0.05$, ##$P<0.01$, ###$P<0.001$)

(Compared with normal control group, ***$P<0.001$; Compared with the model group, ##$P<0.01$, ###$P<0.001$)

DETAILED EMBODIMENTS

The following examples and pharmacological activity test examples are used to further illustrate the present invention, but this does not mean any limitation to the present invention.

The experimental methods in the following examples and pharmacological activity test examples are conventional methods unless otherwise specified; the experimental materials used, unless otherwise specified, are purchased from conventional biochemical reagent companies.

Example 1 Shake Flask Fermentation to Prepare Protein BD-4 Crude Solution a (Tb Medium)

Synthesize the nucleotide sequence shown in SEQ ID NO: 2 and transfer it into the 15 pET-28a(+) vector; confirm the sequence to obtain an expression vector containing the correct sequence; transfect the expression vector into BL21 (DE3) cells, Obtain expression competent host cells containing the target nucleotide sequence. Add LB medium and incubate in a shaker at 37° C. and 220 rpm for 1 hour to obtain a recombinant strain.

Dip the recombinant strain into an LBA plate containing Kanamycin, and place the plate upside down in a 37° C. constant temperature incubator overnight for 16 hours.

Configure 400 ml of TB medium, divided into 2 bottles, each bottle of 200 ml.

Add Kanamycin (final concentration 50 μg/ml) to each bottle (200 ml) of TB medium. Take a single colony on the plate and add it to the TB medium. Amplify and culture overnight at 37° C. and 220 rpm to obtain seed liquid in the shaker.

Configure 28.8 L TB medium, divided into 144 bottles, each bottle of 200 ml. Add Kanamycin (final concentration 50 μg/ml) to each bottle (200 ml) of TB medium, then add 2 ml of seed solution, and incubate in a shaker at 37° C. and 220 rpm for 2-3 hours. Monitor the OD600, when the OD600 reaches about 1.0, add an inducer to induce protein expression in a shaker, and the induction conditions are selected from the following table.

|  | Inducer | Induction temperature | Induction time | Shaker speed |
|---|---|---|---|---|
| Inducing conditions | IPTG(Final concentration 0.5 mM) | 16° C. 25° C. 37° C. | 16 h 8 h 5 h | 220 rpm |

Combine each bottle of bacterial liquid, centrifuge at 7000 rpm for 5 minutes, and discard the supernatant after sterilization; The precipitate is suspended in about 3 L of buffer, filtered with an 80-100 mesh screen, and the filtrate is crushed with a high-pressure crusher at a pressure of 800-1000 bar, twice, 2 minutes each time. Centrifuge the broken bacteria liquid at 7000 rpm for 30 minutes, discard the supernatant, and obtain the precipitate (ie inclusion body). The pellet was washed twice with 1 L detergent, centrifuged and the supernatant was discarded. The precipitate was dissolved in urea solution 4 times, respectively, 800 ml, 600 ml, 400 ml and 400 ml. The four solutions were combined and centrifuged at 7000 rpm for 30 minutes. the precipitate was discarded and the supernatant was the crude protein solution A.

| Buffer | detergent | Urea solution |
|---|---|---|
| buffer A | 2M urea solution (may contain Triton) 4M urea solution (may contain Triton) 2MGuanidine Hydrochloride Solution 4MGuanidine Hydrochloride Solution | 8M urea solution (can contain Tris/HCl buffer or $NaH_2PO_4/Na_2HPO_4$ Buffer) 4M urea solution(can contain Tris/HCl buffer) |

Protein BD-4 crude solution A was analyzed by reduced SDS-PAGE. the separation gel concentration was 12.5% and then stained with Coomassie brilliant blue R250 method; a clear blue band is shown near the molecular weight of 45 kD.

Example 2 Shake Flask Fermentation to Prepare Protein BD-4 Crude Solution B (Other Medium)

In Example 1, it was synthesized and sequenced to confirm that an expression vector containing the sequence shown in SEQ ID NO: 2 was obtained; The expression vector is transfected into Transetta (DE3) cells to obtain expression-competent host cells containing the target nucleotide sequence.

Prepare 20 ml of LB medium, take 800 µl, add 50 µl of host cells containing the target coding sequence, and incubate at 37° C. and 220 rpm for 1 hour in a shaker.

Dip the above bacterial liquid and streak it in an LBA plate containing Kanamycin, and place the plate upside down in a 37° C. constant temperature incubator overnight for 16 hours.

Take 10 ml of LB medium, add Kanamycin (final concentration 50 µg/ml), take a single colony on the plate and add it to the LB medium. Amplify and culture overnight at 37° C. and 220 rpm for 15 hours to obtain seed liquid in a shaker.

Configure 1 L of the medium shown in the table below, and divide it into 10 bottles of 100 ml each. Add Kanamycin (final concentration 50 µg/ml) to each bottle (100 ml) of medium and then add 1 ml of seed solution. Incubate at 37° C. and 220 rpm for 2-3 hours in a shaker. Monitor $OD_{600}$ and add inducer IPTG (final concentration 0.5 mM) when $OD_{600}$ reaches about 1.0. Induce protein expression at 37° C. and 220 rpm in a shaker.

| Culture medium | LB medium, SOB medium, SOC medium |
| --- | --- |

Combine each bottle of bacterial liquid, centrifuge at 10000 rpm for 10 minutes, and discard the supernatant after sterilization; The precipitate is suspended in about 100 mL of buffer, filtered with an 80-100 mesh screen, and the filtrate is crushed with a high-pressure crusher at a pressure of 800-1000 bar, twice, 2 minutes each time. Centrifuge the broken bacteria liquid at 10000 rpm for 30 minutes and discard the supernatant.

Add 40 mL of cleaning agent buffer A to the precipitate for 3 times, centrifuge and discard the supernatant; Add 40 mL of detergent 2M urea solution to the precipitate to wash twice, centrifuge, and discard the supernatant; The precipitate is then added to 8M urea solution (containing 50 mM Tris/HCl buffer) to dissolve 3 times, respectively, 40 ml, 30 ml, 30 ml; The combined solutions were centrifuged at 7000 rpm for 30 minutes, the precipitate was discarded, and the supernatant was the crude protein solution B.

Protein BD-4 crude solution B was analyzed by reduced SDS-PAGE. the separation gel concentration was 12.5% and then stained with Coomassie brilliant blue R250 method; a clear blue band is shown near the molecular weight of 45 kD.

Example 3 Preparation of Crude Protein BD-4 Solution C in a Fermenter

In 5 Example 1, it was synthesized and sequenced to confirm that an expression vector containing the sequence shown in SEQ ID NO: 2 was obtained; The expression vector is transfected into BL21 (DE3) cells to obtain expression-competent host cells containing the target nucleotide sequence. Add LB medium and incubate in a shaker at 37° C. and 220 rpm for 1 hour to obtain a recombinant strain.

In the LBA plate containing Kanamycin, add 100 µl of the recombinant strain, spread the spreader until it becomes evenly dry, and place the plate upside down in a constant temperature incubator at 37° C. for overnight culture. Take three single colonies, streak them on a plate containing Kanamycin, and then culture the plate overnight. After three batches of shake flask fermentation and expression verification are confirmed to be correct, the strains are preserved with 15% glycerol and divided into 0.8 ml each to obtain a working cell bank, which is stored in a refrigerator at −80° C. for later use.

Take out 1 glycerol bacteria from the working cell bank, take 100 µl, add 40 ml LB medium, add Kanamycin (final concentration 50 µg/ml), incubate in a shaker at 37° C. and 220 rpm for 6 hours to obtain a first-level seed solution.

Take 1.2 ml of the first-level seed solution, add it to 120 ml LB medium, add Kanamycin (final concentration 50 µg/ml), and then incubate in a shaker at 37° C. and 220 rpm for 6 hours to obtain a first-level seed solution.

Take 1.2 ml of the first-level seed solution, add 120 ml of LB medium, add Kanamycin (final concentration 50 µg/ml), and then incubate in a shaker at 37° C. and 220 rpm for 7 hours to obtain the second-level seed solution.

Add 3 L of modified LB broth to a 5 L fermentor, then add 120 ml of secondary seed solution, 3 ml of Kanamycin (final concentration 50 µg/ml), and cultivate approximately at 37° C. and 30% dissolved oxygen (series speed) for 8 hours.

Monitor the OD value around 20 and 3 g lactose as an inducer. Induction was performed at 20° C., fed at a rate of 30 ml/hour, and incubated at 20° C. for 24 hours.

Centrifuge the bacterial solution at 7000 rpm for 5 minutes, and discard the supernatant after sterilization; The precipitate is suspended in about 200 mL of buffer A, filtered with an 80-100 mesh screen, and the filtrate is crushed with a high-pressure crusher at a pressure of 800-1000 bar, twice, 2 minutes each time. Centrifuge the broken bacteria liquid at 7000 rpm for 30 minutes and discard the supernatant.

Add 2M urea solution (including 1% Triton) to the precipitate and wash it twice, 1 L each time; Then add 1 L 2M urea solution to wash once, centrifuge and discard the supernatant.

The precipitate is then added to 8M urea solution (containing 50 mM Tris/HCl buffer) to dissolve 4 times, respectively, 400 ml, 300 ml, 200 ml, 100 ml; The four solutions were combined, centrifuged at 7000 rpm for 30 minutes, the precipitate was discarded, and the supernatant was the crude protein solution C.

Protein BD-4 crude solution C was analyzed by reduced SDS-PAGE. the separation gel concentration was 12.5% and then stained with coomassie brilliant blue R250 method; a clear blue band is shown near the molecular weight of 45 kD.

Example 4 Protein Crude Solution C was Prepared by Membrane Technology to Obtain Protein BD-4

The crude protein solution C obtained in Example 3 was purified by microfiltration membrane technology: firstly use a 1500 nm or 1000 nm ceramic membrane core for solid-liquid separation; discard the inner liquid, and then use a 20 nm or 50 nm ceramic membrane core for the outer liquid Repeated microfiltration to remove urea; the inner liquid of the second microfiltration was freeze-dried to obtain the target protein BD-4; the purity determined by electrophoresis was 95.6%
Confirmation of Protein BD-4 Structure:
1、Reduced SDS-polyacrylamide gel electrophoresis (SDS-PAGE) analysis
  Instrument: Protein electrophoresis (Bio-Rad).
  Methods and results: The protein BD-4 solution was analyzed by reduced SDS-PAGE, the separation gel concentration was 12.5%, and it was stained with Coomassie brilliant blue R250 method. The molecular weight of BD-4 band is around 45 kD.
2、Complete protein sequence analysis based on LC-MS/MS
  Main materials: Acetonitrile, formic acid, ammonium bicarbonate, dithiothreitol (DTT), iodoacetamide (IAA), trypsin, chymotrypsin, Glu-C, Asp-N;
  Main instruments: Capillary High Performance Liquid Chromatograph (Thermo Ultimate 3000), Electrospray-Combined Ion Trap Orbitrap Mass Spectrometer (Thermo Q Exative Hybrid Quadrupole-Orbitrap Mass Spectrometer).
  Methods and Results:
  Protein BD-4 undergoes pre-treatments such as dissolution replacement, reductive alkylation, and various proteolysis to obtain enzyme-cleaved peptides; Restriction digestion peptide solution and analyzed by liquid chromatography tandem mass spectrometry. Use Maxquant (1.6.2.10) to search the protein database analysis data of the original mass spectrometry file. The coverage of the identification results was 100%, and it was determined to be consistent with the target sequence SEQ ID NO: 1.

Example 5 Protein Crude Solution A is Purified to Prepare Protein BD-4

The crude protein solution A obtained in Example 1 was purified by the following three methods:
The first method: dialysis;
The crude protein solution A was filtered with a 0.45 μm 1 filter membrane, and the filtrate was combined. The filtrate was dialyzed with dialysis bag water with a molecular weight cut-off of 10 kD, dialyzed for 72 hours, and the inner liquid was freeze-dried to obtain the target protein BD-4; The purity measured by electrophoresis was 90.1%.
The second method: salting out;
The crude protein solution A is placed in a stirred container for two salting out: Slowly add saturated ammonium sulfate solution along the wall to make the final concentration of ammonium sulfate 25% or 50%, During the salting-out process, the protein is separated out. After the salting-out is complete, filter to complete the first salting-out; Add 400 ml of pure water to the precipitate to suspend, and then slowly add a saturated solution of ammonium sulfate along the wall to make the final concentration of ammonium sulfate 25%. Carry out the second salting out, filtration, and the precipitate is the crude protein extract. The crude protein extract was washed three times with water: add 200 ml of pure water to suspend, stir, let stand, and filter; After this is repeated three times, the precipitate is freeze-dried to obtain the target protein BD-4.
The third method: column chromatography;
The crude protein solution A is purified by anion exchange resin column, such as HiTrap Q FF 16/10, HiTrap Capto Q ImpRes, Capto Q ImpRes, HiTrap Capto Q, HiTrap DEAE, etc. The eluent is a gradient elution of NaCl solution, plus 20 mM $NaH_2PO_4/Na_2HPO_4$ buffer (pH 8.0). The elution fractions are combined according to the results of SDS-PAGE electrophoresis detection, The combined eluate was centrifuged twice at 7000 rpm for 1 hour each time; The supernatant was filtered with a 0.45 μm filter membrane, and the filtrates were combined. The filtrates are concentrated by dialysis with water, the molecular weight cut-off of the dialysis bag is 10 kD, and the inner liquid is freeze-dried to obtain the target protein BD-4.
The product protein BD-4 obtained by the three methods was confirmed to have the same amino acid sequence as the protein prepared in Example 4 through the same structural confirmation method as in Example 4.

Example 6 Protein Crude Solution B Purified to Prepare Protein BD-4

The crude protein solution B obtained in Example 2 was purified by the following three methods:
The first method; dialysis;
The crude protein solution B is filtered with a 0.45 μm membrane, the filtrate is dialyzed with water, dialyzed for more than 72 hours, and the inner solution is freeze-dried to obtain the target protein BD-4.

| Dialysis bag | Molecular weight cutoff: 0.5 kD, 3.5 kD, 5 kD, 10 kD |
|---|---|

The second method: column chromatography;
The crude protein solution B is purified by anion exchange resin column, such as HiTrap Q FF 16/10, HiTrap Capto Q ImpRes, Capto Q ImpRes, HiTrap Capto Q, HiTrap DEAE, etc. The eluent is a gradient elution of NaCl solution, plus 20 mM $NaH_2PO_4/Na_2HPO_4$ buffer (pH 8.0). The elution fractions are combined according to the results of SDS-PAGE electrophoresis detection, The combined eluate was centrifuged twice at 7000 rpm for 1 hour each time; The supernatant was filtered with a 0.45 μm filter membrane, and the filtrates were combined. The filtrates are concentrated by dialysis with water, the molecular weight cut-off of the dialysis bag is 10 kD, and the inner liquid is freeze-dried to obtain the target protein BD-4.
The third method: salting out;
The crude protein solution B is placed in a stirred container for two salting out: Slowly add saturated ammonium sulfate solution along the wall to make the final concentration of ammonium sulfate 25% or 50%, During the salting-out process, the protein is separated out. After the salting-out is complete, filter to complete the first salting-out; Add 400 ml of pure water to the precipitate to suspend, and then slowly add a saturated solution of ammonium sulfate along the wall to make the final concentration of ammonium sulfate 25%. Carry out the second salting out, filtration, and the precipitate is the crude protein extract. The crude protein extract was washed three times with water: add 200 ml of pure water to suspend, stir, let stand, and filter; After this is repeated three times, the precipitate is freeze-dried to obtain the target protein BD-4.
The product protein BD-4 obtained by the three methods was confirmed to have the same amino acid sequence as the protein prepared in Example 4 through the same structural confirmation method as in Example 4.

Example 7 Crude Protein Solution C Purified to Prepare Protein BD-4 by Salting-Out Method The crude protein solution C obtained in Example 3 was placed in a container with stirring for two salting out: Slowly add saturated ammonium sulfate solution along the wall to make the final concentration of ammonium sulfate 25% or 50%, During the salting-out process, the protein is separated out. After the salting-out is complete, filter to complete the first salting-out; Add 400 ml of pure water to the precipitate to suspend, and then slowly add a saturated solution of ammonium sulfate along the wall to make the final concentration of ammonium sulfate 25%. Carry out the second salting out, filtration, and the precipitate is the crude protein extract. The crude protein extract was washed three times with water: add 200 ml of pure water to suspend, stir, let stand, and filter; After this is repeated three times, the precipitate is freeze-dried to obtain the target protein BD-4.

The product protein BD-4 obtained to have the same amino acid sequence as the protein prepared in Example 4 through the same structural confirmation method as in Example 4.

Pharmacological Test

Experimental example 1 The pharmacodynamic test of protein BD-4 (the protein in Example 4) on the fever model of SD rats induced by yeast Animals: 230-260 grams of male SD rats;
Medicines: yeast (OXOID LP0021), aspirin (SIGMA A2093), protein BD-4;
Instruments: electronic balance (SARTORIUS BP121S type), electronic clinical thermometer (CITIZEN CT-513W type).

Experiment Grouping:
Normal control group;
Model group: yeast fever model;
Positive control group: Aspirin 300 mg/kg group;
Protein BD-4, 10 mg/kg group, 50 mg/kg group.

Method:

Preparation of experimental animals: After the experimental animals adapt to the experimental environment (temperature 22° C.±2° C., relative humidity 50%±2%) for 1 day. Pre-adaptation to measure rectal temperature at 8:00 and 15:00, Rats were fasted and water was taken freely 12 h before experiment. let the animal to empty its feces before measuring the rectal temperature. Apply petroleum jelly to the electronic thermometer probe before each temperature measurement. Insert the rat rectum 2 cm (can be marked at 2 cm to ensure that the depth of each insertion is consistent), and record the body temperature after the reading is stable.

Subcutaneous injection of dry yeast to replicate rat fever model: The body temperature of the rats was measured before modeling. Qualified rats with a body temperature of 36.2-37.3° C. were selected and randomly divided into groups with 8 rats in each group. After oral administration of aspirin and different doses of protein BD-4, 20% yeast suspension (10 ml/kg) was injected subcutaneously immediately, and the normal control group was injected intraperitoneally with an equal volume of normal saline. the rats' body temperature was monitored after 2 hours for a total of 8 hours.

Statistics:

According to the body temperature measured at each time point on the day of the experiment, calculate the mean, standard deviation and standard error of the body temperature of each group of rats. The data of each group was compared with TTEST, and P<0.05 was considered as a significant difference.

Figures 1, 2:
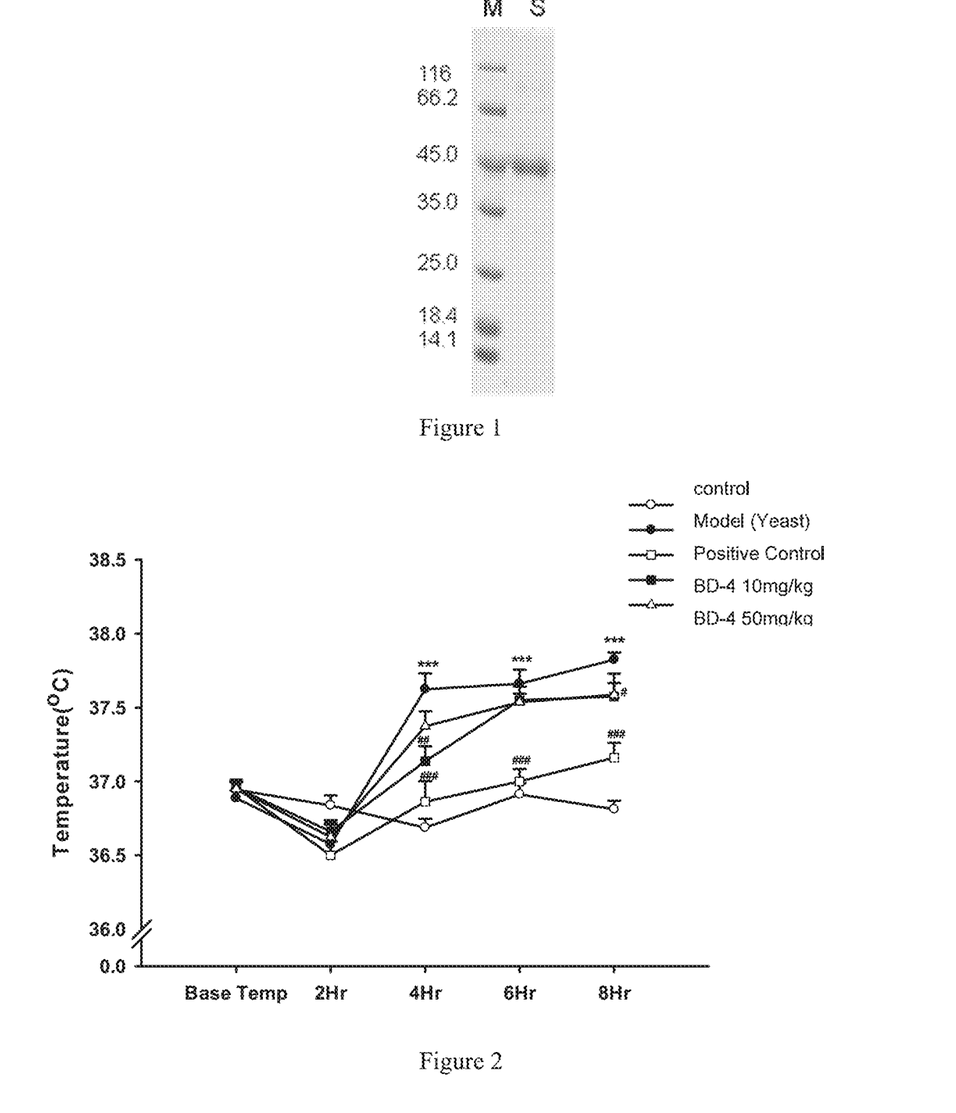
FIG. 1: Analysis of expressed protein BD-4 reduced SDS polyacrylamide gel electrophoresis (SDS-PAGE).
FIG. 2: Effect of protein BD-4 on yeast-induced fever model in rats.

Experimental Results:

After oral administration of aspirin (300 mg/kg), protein BD-4 (10 mg/kg, 50 mg/kg), immediately subcutaneous injection of 20% yeast model. The animal body temperature was monitored at 2 hours, 4 hours, 6 hours, and 8 hours after modeling. The results are shown in Table 1 and FIG. 2.

TABLE 1

Effects of the tested drugs on the yeast-induced fever model in rats

| Group | N | Basal body temperature(° C.) | Body temperature 2 hours after modeling(° C.) | Body temperature 4 hours after modeling(° C.) | Body temperature 6 hours after modeling(° C.) | Body temperature 8 hours after modeling(° C.) |
| --- | --- | --- | --- | --- | --- | --- |
| Normal control group | 8 | 36.9 ± 0.1 | 36.8 ± 0.1 | 36.7 ± 0.1 | 36.9 ± 0.1 | 36.8 ± 0.1 |
| Model group | 8 | 36.9 ± 0.05 | 36.6 ± 0.1 | 37.6 ± 0.1*** | 37.7 ± 0.1*** | 37.8 ± 0.05*** |
| Positive control group | 8 | 37.0 ± 0.1 | 36.5 ± 0.1 | 36.9 ± 0.1### | 37.0 ± 0.1### | 37.2 ± 0.1### |
| BD-4-10 mg/kg | 8 | 37.0 ± 0.1 | 36.7 ± 0.1 | 37.1 ± 0.1## | 37.6 ± 0.1 | 37.6 ± 0.2 |
| BD-4-50 mg/kg | 8 | 37.0 ± 0.05 | 36.6 ± 0.1 | 37.4 ± 0.1 | 37.5 ± 0.1 | 37.6 ± 0.1# |

(Compared with the normal control group,
** P < 0.01,
*** P < 0.001; compared with the model group,
# P < 0.05,
## P < 0.01,
### P < 0.001)

Experimental Results:

oral administration of aspirin (300 mg/kg) and protein BD-4 (10 mg/kg, 50 mg/kg), 20% yeast was injected injected subcutaneously immediately to make the model. Monitor the animal's body temperature at 2 hours, 4 hours, 6 hours, and 8 hours after making the model. The results show that:

1) The body temperature of rats in the model group increased significantly at 4 hours, 6 hours, and 8 hours after modeling. Compared with the normal group, $P<0.05$, which was statistically different. The model was successfully established and was stable and reliable.

2) The positive drug aspirin group can effectively inhibit the increase in body temperature of model rats at 4 hours, 6 hours, and 8 hours after modeling. Compared with the model group, $P<0.05$, there is a statistical difference, and the performance of positive tool drugs is relatively stable.

3) Protein BD-4 10 mg/kg dose group can significantly inhibit the increase in body temperature of model rats 4 hour after modeling. Compared with the model group, $P<0.05$, there is a statistical difference. The 50 mg/kg dose group can significantly inhibit the increase in body temperature of the model rats 8 hours after modeling, and compared with the model group, $P<0.05$, there is a statistical difference.

Experimental example 2 The pharmacodynamic test of protein BD-4 (Example 4 protein) on lipopolysaccharide (LPS) induced fever in SD rats.

Animals: 230-260 grams of male SD rats;

Drugs: lipopolysaccharide (LPS, SIGMA L-2880), aspirin (SIGMA A2093), protein BD-4;

Instruments: electronic balance (SARTORIUS BP121S type), electronic clinical thermometer (CITIZEN CT-513W type).

Experiment Grouping:
Model group: lipopolysaccharide fever model;
Positive control group: Aspirin 300 mg/kg group,
Protein BD-4, 10 mg/kg group, 50 mg/kg group.

Method: the method of intraperitoneal injection of Lipopolysaccharide to create fever model in rats.

Preparation of experimental animals: After the experimental animals adapt to the experimental environment (temperature 22° C.±2° C., relative humidity 50%±2%) for 1 day. Pre-adaptation to measure rectal temperature at 8:00 and 15:00, Rats were fasted and water was taken freely 12 h before experiment. before the experiment, let the animal to empty its feces before measuring the rectal temperature. Apply petroleum jelly to the electronic thermometer probe before each temperature measurement. Insert the rat rectum 2 cm (can be marked at 2 cm to ensure that the depth of each insertion is consistent), and record the body temperature after the reading is stable.

Intraperitoneal injection of lipopolysaccharide to replicate rat fever model: The body temperature of the rats was measured before modeling. Qualified rats with a body temperature of 36.2-37.3° C. were selected and randomly divided into groups with 8 rats in each group. After oral administration of aspirin and different doses of protein BD-4, lipopolysaccharide (20 μg/kg, 2 ml/kg) was injected intraperitoneally immediately, and the normal control group was injected intraperitoneally with an equal volume of normal saline. the rats' body temperature was monitored after 2 hours for a total of 8 hours.

Statistics:

According to the body temperature measured at each time point on the day of the experiment, calculate the mean, standard deviation and standard error of the body temperature of each group of rats. The data of each group was compared with TTEST, and $P<0.05$ was considered as a significant difference.

Figure 3:
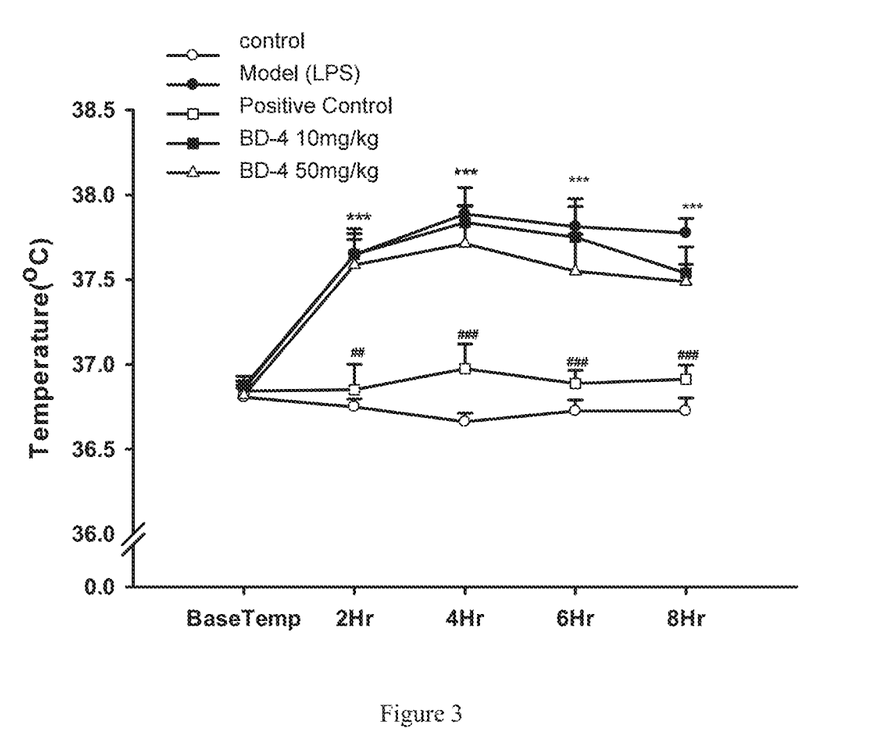
FIG. 3: Effect of protein BD-4 on lipopolysaccharide (LPS) induced fever in rats.

Experimental Results:

After oral administration of aspirin (300 mg/kg), protein BD-4 (10 mg/kg, 50 mg/kg), immediately intraperitoneal injection of 20 μg/kg lipopolysaccharide model. The animal body temperature was monitored at 2 hours, 4 hours, 6 hours, and 8 hours after modeling. The results are shown in Table 2 and FIG. 3.

TABLE 2

Effects of test drugs on lipopolysaccharide (LPS) induced fever in rats

| Group | N | Basal body temperature(° C.) | Body temperature 2 hours after modeling(° C.) | Body temperature 4 hours after modeling(° C.) | Body temperature 6 hours after modeling(° C.) | Body temperature 8 hours after modeling (° C.) |
|---|---|---|---|---|---|---|
| Normal control group | 8 | 36.8 ± 0.1 | 36.8 ± 0.05 | 36.7 ± 0.05 | 36.7 ± 0.1 | 36.7 ± 0.1 |
| Model group | 8 | 36.9 ± 0.04 | 37.7 ± 0.2*** | 37.9 ± 0.2*** | 37.8 ± 0.2*** | 37.8 ± 0.1*** |
| Positive control group | 8 | 36.8 ± 0.1 | 36.9 ± 0.2## | 37.0 ± 0.1### | 36.9 ± 0.1### | 36.9 ± 0.1### |
| BD-4-10 mg/kg | 8 | 36.9 ± 0.1 | 37.7 ± 0.1 | 37.8 ± 0.1 | 37.8 ± 0.2 | 37.5 ± 0.2 |
| BD-4-50 mg/kg | 8 | 36.8 ± 0.1 | 37.6 ± 0.2 | 37.7 ± 0.2 | 37.6 ± 0.2 | 37.5 ± 0.1 |

(Compared with the normal control group,
***$P < 0.001$; compared with the model group,
$P < 0.01$,
$P < 0.001$)

Experimental Results:

oral administration of aspirin (300 mg/kg) and protein BD-4 (10 mg/kg, 50 mg/kg), 20 μg/kg lipopolysaccharide was injected into the intraperitoneal cavity immediately to make the model. Monitor the animal's body temperature at 2 hours, 4 hours, 6 hours, and 8 hours after making the model. The results show that.

1) Intraperitoneal injection of 20 μg/kg lipopolysaccharide can successfully induce the increase of body temperature in rats. The body temperature of rats in the model group increased significantly at 2 hours, 4 hours, 6 hours, and 8 hours after modeling. Compared with the normal group, $P<0.05$, there is a statistical difference, and the model is stable.

2) The positive drug aspirin group can effectively inhibit the increase in body temperature of model rats at 2 hours, 4 hours, 6 hours, and 8 hours after modeling. Compared with the model group, P<0.05, there is a statistical difference, and the performance of positive tool drugs is relatively stable.

3) Protein BD-4 has a tendency to lower the body temperature of model rats after modeling, but it is not statistically significant.

Experimental example 3 The pharmacodynamic test of protein BD-4 (Example 4 protein) on convulsive epilepsy in mice caused by the convulsion agent Pilocarpine (PLO)

Animals: male ICR mice;

Drugs: Pilocarpine HCl (PLO, pilocarpine, pilocarpine hydrochloride), Diazepam (diazepam tablets), protein BD-4.

Experiment Grouping:
 Model group:
 Diazepam (Diazepam) 2 mg/kg group;
 Protein BD-4, 50 mg/kg group, 200 mg/kg group.

Method:

Model Preparation and Administration:

The drug was administered once in the afternoon the day before modeling, PLO-225 mg/kg (modeling agent) was injected intraperitoneally 1 hour after the test drug was given to the stomach on the day of modeling. And positive drug can be administered once 20 minutes before modeling. Observe for 30 minutes after PLO injection.

Observation indicators: 1) Seizure situation: the time of seizures from grade II to grade IV; 2) the time to death.

Attack level: Refer to Racine grading standard: Level 0: No response; Grade I: manifested as twitching of facial muscles or the corners of the mouth; Level II: can nod; Level III: Twitching of one limb; Grade IV: rigidity or body twitching; Grade V: generalized epilepsy (generalized tonic seizures).

Data Processing:

Count the number of grade IV seizures and deaths in each group of mice in the experiment; Level II, III and IV incubation period. The incubation period of mice that did not attack to grade IV was recorded as a maximum of 1800 seconds. Chi-square test was used for statistics of the number of cases. The mean value and standard error of the incubation period were calculated, and TTEST was used to compare the model group with other groups. $P<0.05$ was considered as a significant difference.

Experimental results; see Table 3 and Table 4.

TABLE 3

Experiments of tested drugs on PLO-induced epilepsy in mice-statistics of cases

| Group | Number of experimental examples | Number of Grade IV cases | Grade IV seizure rate | Number of deaths | mortality rate |
|---|---|---|---|---|---|
| Model group | 10 | 7 | 70% | 1 | 10% |
| Diazepam 2 mg/kg | 10 | 0** | 0** | 0 | 0 |
| BD-4-50 mg/kg | 10 | 7 | 70% | 0 | 0 |
| BD-4-200 mg/kg | 10 | 9 | 90% | 1 | 10% |

(Compared with the model group, *P < 0.05, **P < 0.01)

TABLE 4

Experiments of tested drugs on PLO-induced epilepsy in mice-
Level II, Level III and Level IV seizure latency (mean ± SEM)

| Group | Level II onset incubation period (s) | Level III onset incubation period (s) | Level IV onset incubation period (s) |
|---|---|---|---|
| Model group | 82 ± 4 | 124 ± 5 | 958 ± 205 |
| Diazepam 2 mg/kg | 118 ± 9** | 172 ± 13** | 1800 ± 0** |
| BD-4-50 mg/kg | 95 ± 3* | 162 ± 5** | 974 ± 192 |
| BD-4-200 mg/kg | 95 ± 6 | 184 ± 17** | 765 ± 135 |

(Compared with the model group, *P < 0.05, **P < 0.01)

Experimental Results:
1) Experimental results show that the rate of grade IV attacks in the model group is 70%. 2 out of 40 mice died.
2) Positive drugs can completely suppress the rate of grade IV epileptic seizures and significantly prolong the incubation period of grade II, III and IV seizures in mice.
3) In the comparison of epilepsy grade II incubation period, the BD-4 50 mg/kg dose groups were statistically different from the model group; In the comparison of epilepsy grade III incubation period, the BD-4 50 mg/kg and 200 mg/kg dose groups were statistically different from the model group;

Experimental example 4 Efficacy test of protein BD-4 (Example 4 protein) on pentylenetetrazole (PTZ)-induced epilepsy in mice
Animals: male ICR mice;
Medicines: Pentylenetetrazol (PTZ), Retigabine, Protein BD-4.
Experiment Grouping:
  Model group;
  Retigabine 60 mg/kg group;
  Protein BD-4, 50 mg/kg group, 200 mg/kg group;
Method:
Model Preparation and Administration:
  Administer once in the afternoon the day before modeling, On the day of modeling, intraperitoneal injection of PTZ-65 mg/kg (modeling agent) 1 hour after gavage of the test drug, the positive drug can be administered once half an hour before modeling. Continue to observe for 15 minutes after injection of PTZ.
  Observation index: 1) Seizure condition: Onset time of grade III to grade VI; 2) Death situation
  Onset level: Refer to Racine grading standard: Level 0: No response; Grade I: manifested as twitching of facial muscles or the corners of the mouth; Level II: Can nod; Grade III: twitching of one limb; Grade IV: Rigidity or body twitching; Grade V: Generalized epilepsy (Generalized tonic seizures).
Data Processing:
  Count the number of seizures and deaths in each group of mice in the experiment; Level III and IV incubation period. The incubation period of mice that have not attacked to grade IV is recorded as the maximum of 900 seconds. Chi-square test was used for statistics of the number of cases. Calculate the mean and standard error of the incubation period. Use TTEST to compare the model group with other groups, and P<0.05 is considered as a significant difference.
Experimental results: see Table 5 and Table 6.

TABLE 5

Test drug on PTZ-induced epilepsy in mice-statistics of cases

| Group | Number of experimental examples | Number of Grade IV cases | Grade IV seizure rate | Number of deaths | mortality rate |
|---|---|---|---|---|---|
| Model group | 10 | 9 | 90% | 2 | 20% |
| Retigabine 60 mg/kg | 10 | 1** | 10%** | 0 | 0 |
| BD-4-50 mg/kg | 10 | 8 | 80% | 1 | 10% |
| BD-4-200 mg/kg | 10 | 7 | 70% | 0 | 0 |

(Compared with the model group, *P < 0.05, **P < 0.01)

TABLE 6

Experiment of the test drug on PTZ-induced epilepsy in mice-the incubation period of grade III and IV seizures (mean ± SEM)

| Group | Level III onset latency (s) | Grade IV onset latency (s) |
|---|---|---|
| Model group | 63 ± 6 | 211 ± 81 |
| Retigabine 60 mg/kg | 106 ± 12** | 819 ± 81** |
| BD-4-50 mg/kg | 91 ± 12* | 308 ± 103 |
| BD-4-200 mg/kg | 89 ± 8** | 493 ± 113 |

(Compared with the model group, *P < 0.05, **P < 0.01)

Experimental Results:
1) The experimental results showed that the grade IV attack rate in the model group was 90%. Three of the 40 mice died.
2) Positive drugs can significantly reduce the rate of class IV epileptic seizures, and significantly prolong the incubation period of class III and IV seizures in mice.
3) In the comparison of epilepsy grade III incubation period, the BD-4 50 mg/kg and 200 mg/kg dose groups were statistically different from the model group.

Experimental example 5 The pharmacodynamic test of protein BD-4 (Example 4 protein) on the expectorant of phenol red excretion method in mice.
Animals: male ICR mice;
Drugs and reagents: Mucosultan (ambroxol hydrochloride tablets), phenol red, sodium bicarbonate, protein BD-4;
Instruments: centrifuge (Sigma-3K15 type), balance (XS105DU type), Microplate tester (BIO-TEK type).
Experiment Grouping:
  Solvent control group;
  Mucosultan 30 mg/kg group;
  Protein BD-4, 20 mg/kg group, 50 mg/kg group.
Method:
Model Preparation and Administration:
  The animals were fasted and watered 16 hours before the experiment. Orally administered Mucosultan and different doses of protein BD-4 (administration volume 10 ml/kg) in groups, and the solvent control group was given the same volume of distilled water. One hour later, 2.5% phenol red solution was injected intraperitoneally, Kill the mouse by removing the neck after 30 minutes. Take the trachea from below the thyroid cartilage to the branch of the trachea. Put the trachea into 3 ml 5% NaHCO$_3$ solution and let it stand for 3 hours. Take 1 ml of the supernatant and centrifuge at 3000 rpm for 5 minutes. Measure and record the absorbance at 546 nm. According to the standard curve of phenol red, the excretion of phenol red was calculated.

Data Processing:

Record the time point of oral administration, the time point of intraperitoneal injection of 2.5% phenol red solution, and the time point of tracheal extraction respectively; The absorbance of each group of samples was measured by the microplate reader at 546 nm, Calculate the excretion of phenol red according to the standard curve of phenol red. Calculate the mean and standard error of the data in each group, use TTEST to compare the solvent control group with other groups, and P<0.05 is considered as a significant difference.

Experimental Results:

Give Mucosultan (30 mg/kg) and different doses of protein BD-4 (20 mg/kg, 50 mg/kg). One hour later, 2.5% phenol red solution was intraperitoneally injected, and 30 minutes later, the mice were killed by removing their necks. Take the trachea from below the thyroid cartilage to the branch of the trachea, put the trachea into 3 ml of 5% NaHCO$_3$ solution and let it stand for 3 hours, take 1 ml of supernatant, centrifuge at 3000 rpm for 5 minutes, measure and record the absorbance at 546 nm. According to the standard curve of phenol red, the excretion of phenol red was calculated. The results are shown in Table 7.

TABLE 7

The effect of the test drug on the expectorant effect of the phenol red excretion method in mice (X ± SEM)

| Group | N | Phenol red excretion(μg/ml) | P |
|---|---|---|---|
| Solvent control group | 10 | 0.638 ± 0.088 | — |
| Mucosolvan 30 mg/kg | 10 | 1.138 ± 0.079** | 0.001 |
| BD-4-20 mg/kg | 10 | 0.898 ± 0.076* | 0.038 |
| BD-4-50 mg/kg | 10 | 0.775 ± 0.101 | 0.320 |

(Compared with the solvent control group, *P < 0.05, **P < 0.01)

Experimental Results:
1) The experimental results showed that compared with the solvent control group, the amount of phenol red excretion in the Mucosultan 30 mg/kg group was significantly increased, P<0.05, which was statistically significant.
2) Compared with the solvent control group, the BD-4 20 mg/kg dose groups significantly increased the excretion of phenol red, P<0.05, which was statistically significant.

Experimental example 6 The effect of protein BD-4 (Example 4 protein) on the antitussive effect of the cough induced by ammonia water in mice.

Animals: male ICR mice;
Drugs and reagents: dextromethorphan hydrobromide, ammonia, 0.2% CMC-Na, protein BD-4;
Apparatus: Compressed nebulizer (403T type), balance (XS105DU type).
Experiment Grouping:
  Solvent control group;
  Dextromethorphan 15 mg/kg group;
  Protein BD-4, 20 mg/kg group, 50 mg/kg group.
Method:
Model Preparation and Administration:

Dextromethorphan and different doses of protein BD-4 (administration volume 10 ml/kg) were given orally in groups, and the solvent control group was given the same volume of distilled water. One hour later, it was put into a sealed box and atomized 10% ammonia water for 10 seconds, and then observed and recorded the incubation period of cough in mice and the number of coughs in 2 minutes.

Data Processing:

Record the time point of oral administration, the time point of atomization experiment, the incubation period of mice cough and the number of coughs within 2 minutes, respectively. The incubation period of cough refers to the number of seconds from the start of the atomization of ammonia to the occurrence of cough. The performance of coughing in mice is based on contraction of their abdominal muscles (breast contraction) and opening their mouths at the same time. Calculate the mean and standard error of each group of data, use TTEST to compare the model group with other groups, and P<0.05 is considered as a significant difference.

Experimental Results:

Give dextromethorphan (15 mg/kg) and different doses of protein BD-4 (20 mg/kg, 50 mg/kg) in advance, one hour later, it was put into a sealed box and atomized 10% ammonia water for 10 seconds, and then the mice were observed and recorded the incubation period of coughing and the number of coughs within 2 minutes. The results are shown in Table 8.

TABLE 8

Antitussive effect experiment of tested drugs on mice cough induced by ammonia water (X ± SEM)

| Group | N | Incubation period(s) | P | Number of coughs | P |
|---|---|---|---|---|---|
| Solvent control group | 9 | 25.6 ± 2.4 | — | 74.4 ± 4.1 | — |
| Dextromethorphan 15 mg/kg | 9 | 39.2 ± 2.8** | 0.002 | 40.2 ± 3.5** | 0.001 |
| BD-4-20 mg/kg | 9 | 34.0 ± 2.4* | 0.025 | 55.9 ± 3.5** | 0.003 |
| BD-4-50 mg/kg | 9 | 33.2 ± 3.9 | 0.116 | 62.1 ± 3.7* | 0.039 |

(Compared with the solvent control group, *P < 0.05, **P < 0.01)

Experimental Results:
1) The experimental results showed that the dextromethorphan group and the solvent control group had a significant improvement in the incubation period and the number of coughs, P<0.05, which was statistically significant.
2) The BD-4 20 mg/kg and 50 mg/kg dose groups have a significant improvement in the number of coughs compared with the solvent control group, P<0.05, which is statistically significant; the BD-4 20 mg/kg dose group has a significant improvement in the incubation period. Compared with the solvent control group, there is a significant improvement, P<0.05, which is statistically significant.

Experimental example 7 The pharmacodynamic test of protein BD-4 (Example 4 protein) on acetic acid writhing in ICR mice.

Animals: male ICR mice;
Drugs and reagents: aspirin, physiological saline, glacial acetic acid, protein BD-4.
Experiment Grouping:
  Model group;
  Aspirin 300 mg/kg group;
  Protein BD-4, 50 mg/kg group, 200 mg/kg group.
Method:

One day after the experimental animals adapt to the environment, Aspirin 300 mg/kg, protein BD-4 50 mg/kg, 200 mg/kg were given orally one hour in advance, and the administration volume was 10 ml/kg; Then, 0.6% acetic acid solution was injected into the abdominal cavity, and the latency period (seconds) and frequency of writhing in the animal was observed within 15 minutes.

Data Processing:

Calculate the mean and standard error of the data in each group. Compared with the model group by TTEST, P<0.05 was considered as statistically different.

Experimental Results:

One hour after oral administration of aspirin 300 mg/kg and different doses of protein BD-4 (50 mg/kg, 200 mg/kg), 0.6% acetic acid solution was intraperitoneally injected to observe the writhing latency and frequency of ICR mice. The results are shown in Table 9.

TABLE 9

The effects of the tested drugs on the acetic acid writhing test of ICR mice

| Group | N | Weight (g) | Writhing latency (seconds) | Number of twists (times) |
|---|---|---|---|---|
| Model group 0.6% acetic acid | 22 | 23.8 ± 0.3 | 234.6 ± 26.0 | 29.3 ± 3.6 |
| aspirin 300 mg/kg | 13 | 24.3 ± 0.4 | 301.0 ± 30.4 | 16.7 ± 2.6* |
| BD-4-50 mg/kg | 15 | 24.6 ± 0.2 | 315.2 ± 66.3 | 16.9 ± 3.7* |
| BD-4-200 mg/kg | 13 | 24.4 ± 0.4 | 220.1 ± 16.6 | 25.1 ± 3.3 |

(Compared with the model group, **P < 0.01)

Experimental Results:

0.6% acetic acid solution was injected into the abdominal cavity of mice, which caused deep and large area and long-term painful stimulation, causing the mice to writhe (the abdomen was contracted into an "S" shape, the trunk and hind legs were stretched, the buttocks were raised and the hips Row). The incubation time and the number of times the mice began to writhe were used as the pain response index to determine whether the test sample had analgesic effect. The results of this experiment show:

1) Aspirin 300 mg/kg can significantly delay the incubation period of writhing and reduce the frequency of writhing, and has a certain analgesic effect. Compared with the model group, P<0.05, which is statistically significant.

2) The BD-4 50 mg/kg dose group can significantly reduce the number of writhing times in mice. Compared with the model group, P<0.05, which is statistically significant.

The invention claimed is:

1. A method for antipyretic, analgesic, antitussive, expectorant, anticonvulsant, or antiepileptic, comprising a step of administering to a subject in need thereof with an effective amount of keratin BD-4;
wherein amino acid sequence of the keratin BD-4 is the amino acid sequence shown in SEQ ID NO: 1 in the sequence listing.

2. The method according to claim 1, wherein the keratin BD-4 can be conventionally modified; or a label for detection or purification is also attached to the keratin BD-4.

3. The method according to claim 2, wherein the conventional modification includes acetylation, amidation, cyclization, glycosylation, phosphorylation, alkylation, biotinylation, fluorescent group modification, Polyethylene glycol PEG modification, immobilization modification, sulfation, oxidation, methylation, deamination, formation of disulfide bonds or disulfide bond breakage; the tags include His6, GST, EGFP, MBP, Nus, HA, IgG, FLAG, c-Myc, Profinity eXact.

4. A method for antipyretic, analgesic, antitussive, expectorant, anticonvulsant or antiepileptic, comprising a step of administering to a subject in need thereof with an effective amount of a pharmaceutical composition contains keratin BD-4 and a pharmaceutically acceptable carrier or excipient;
wherein amino acid sequence of the keratin BD-4 is the amino acid sequence shown in SEQ ID NO: 1 in the sequence listing.

5. The method according to claim 4, wherein the keratin BD-4 can be conventionally modified; or a label for detection or purification is also attached to the keratin BD-4.

6. The method according to claim 5, wherein the conventional modification includes acetylation, amidation, cyclization, glycosylation, phosphorylation, alkylation, biotinylation, fluorescent group modification, Polyethylene glycol PEG modification, immobilization modification, sulfation, oxidation, methylation, deamination, formation of disulfide bonds or disulfide bond breakage; the tags include His6, GST, EGFP, MBP, Nus, HA, IgG, FLAG, c-Myc, Profinity eXact.

* * * * *